United States Patent [19]

Russell et al.

[11] Patent Number: 5,512,037
[45] Date of Patent: Apr. 30, 1996

[54] PERCUTANEOUS SURGICAL RETRACTOR

[75] Inventors: Brian G. Russell, Wilsonville, Oreg.;
H. Jonathan Tovey, Milford, Conn.

[73] Assignee: United States Surgical Corporation, Norwalk, Conn.

[21] Appl. No.: 241,927

[22] Filed: May 12, 1994

[51] Int. Cl.$^6$ .................................................. A61B 17/02
[52] U.S. Cl. .......................... 600/206; 600/201; 600/204; 604/51; 606/198
[58] Field of Search ............................... 128/20, 17, 18, 128/3, 4 SM, 772; 606/191, 198, 185, 205; 604/51; 600/201, 204, 206

[56] References Cited

U.S. PATENT DOCUMENTS

| | | |
|---|---|---|
| 987,173 | 3/1911 | Sale . |
| 2,137,710 | 11/1938 | Anderson . |
| 3,467,079 | 9/1969 | James . |
| 3,467,090 | 9/1969 | Zollett . |
| 3,570,498 | 3/1971 | Weighton ............................ 128/20 X |
| 4,190,042 | 2/1980 | Sinnreich ............................ 128/20 |
| 4,393,872 | 7/1983 | Reznik et al. . |
| 4,459,978 | 7/1984 | Kotsanis . |
| 4,654,028 | 3/1987 | Suma . |
| 4,655,219 | 4/1987 | Petruzzi . |
| 4,665,906 | 5/1987 | Jervis . |
| 4,741,330 | 5/1988 | Hayhurst . |
| 4,830,002 | 5/1989 | Semm . |
| 4,874,375 | 10/1989 | Ellison ............................... 128/20 X |
| 4,890,612 | 1/1990 | Kensey . |
| 4,909,789 | 3/1990 | Taguchi . |
| 5,106,369 | 4/1992 | Christmas . |
| 5,151,086 | 9/1992 | Duh et al. . |
| 5,195,505 | 3/1993 | Josefsen . |
| 5,242,456 | 9/1993 | Nash et al. . |
| 5,281,220 | 1/1994 | Blake, III ......................... 606/205 X |
| 5,282,806 | 2/1994 | Haber et al. ..................... 606/205 X |
| 5,300,084 | 4/1994 | Johnson ............................... 606/185 |
| 5,351,679 | 10/1994 | Mayzels et al. ...................... 128/20 |
| 5,352,235 | 10/1994 | Koros et al. ..................... 606/170 X |

FOREIGN PATENT DOCUMENTS

WO91/02493  3/1991  WIPO .

OTHER PUBLICATIONS

Nassif, et al., (PEG) Improvements in: Percutaneous Endoscopic Gastrostomy, Jan. 28–30, 1990.

*Primary Examiner*—Richard J. Apley
*Assistant Examiner*—Beverly M. Flanagan

[57] ABSTRACT

A percutaneous surgical retractor is provided for performing examinations or surgical procedures through the skin. The retractor has an outer sleeve structure with a proximal and an open beveled distal end. A blade is slidable within the outer sleeve and moveable between at least a deployed position and a retracted position. The retracting blade substantially closes the open beveled distal end of the outer sleeve when the blade is in the retracted position to inhibit the coring of tissue by the outer sleeve during percutaneous insertion. The retractor has structure for deploying the retracting blade relative to the outer sleeve.

18 Claims, 4 Drawing Sheets

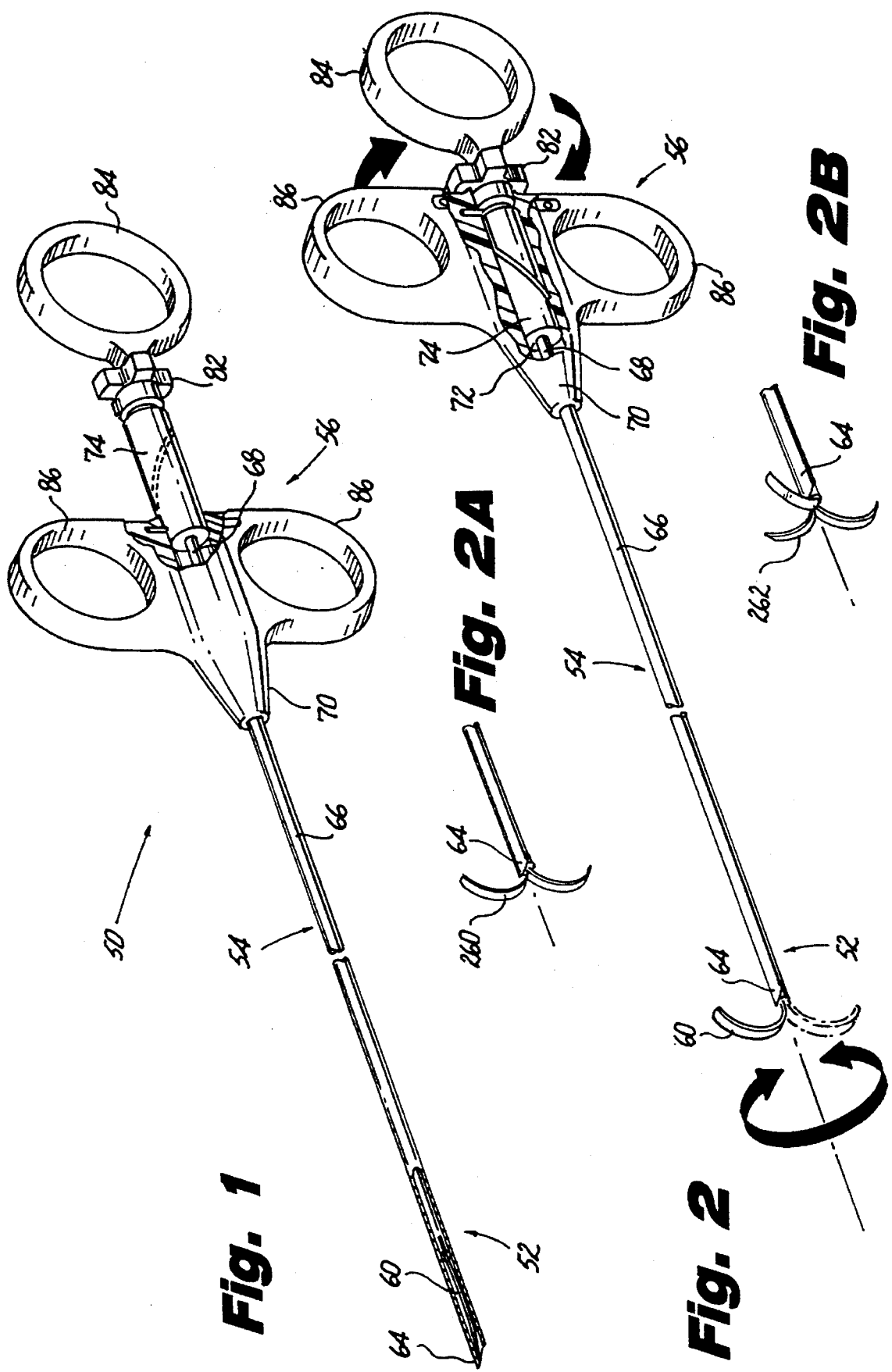

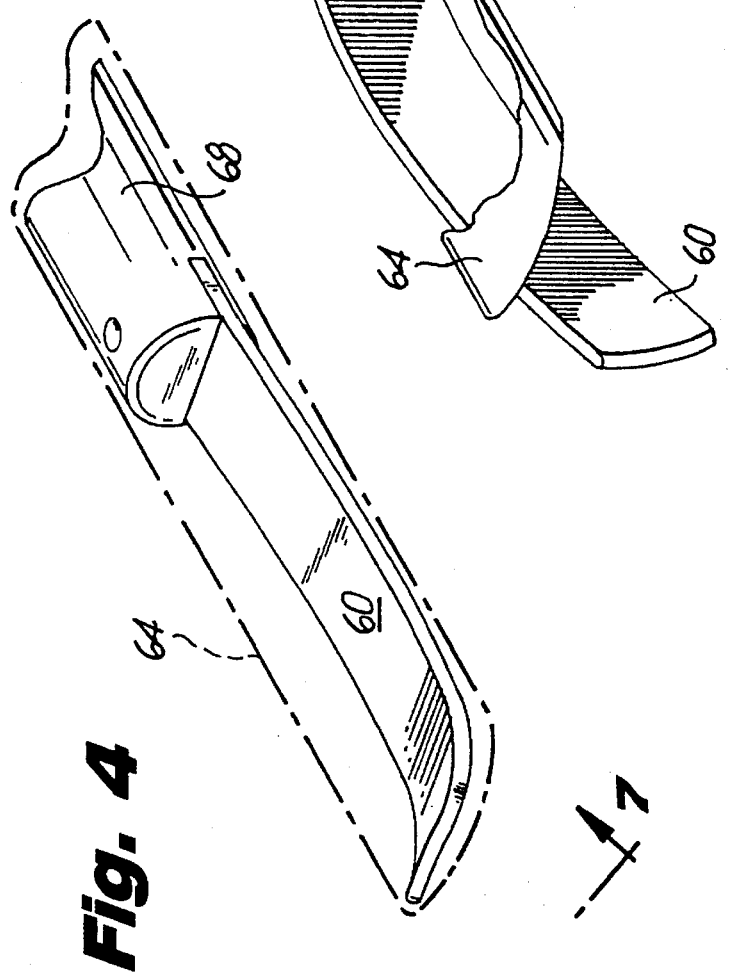
Fig. 4
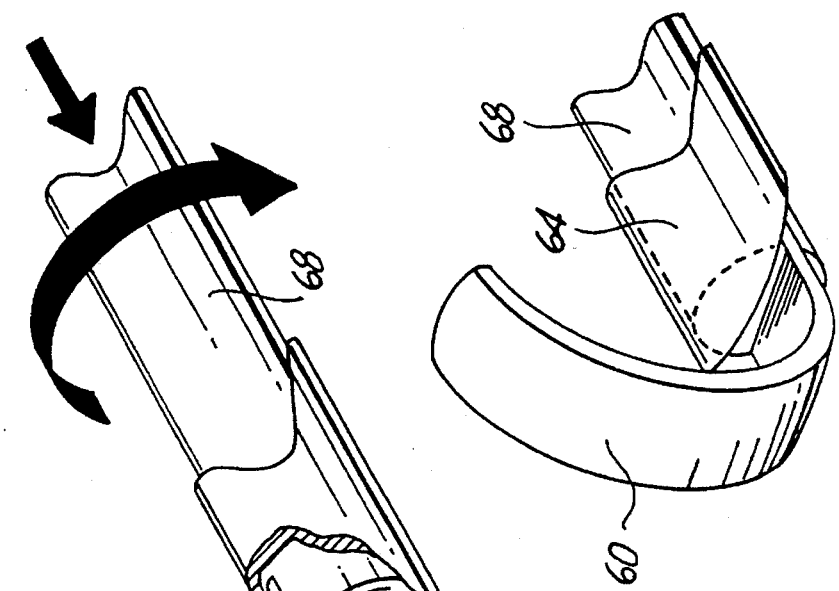
Fig. 5
Fig. 6
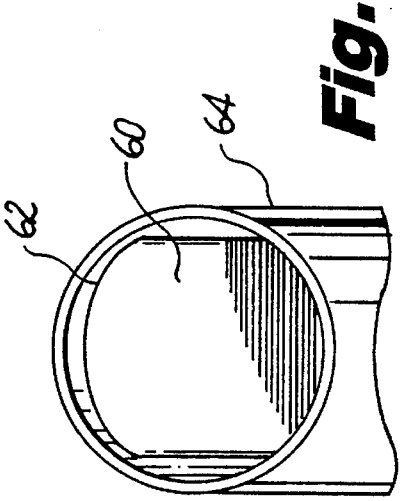
Fig. 7

PERCUTANEOUS SURGICAL RETRACTOR

BACKGROUND OF THE INVENTION

1. Field of the Invention

This invention relates generally to surgical instrumentation and, more particularly, to a surgical retractor adapted for percutaneous introduction in performing examinations or surgical procedures within body cavities.

2. Description of Related Art

During surgery, the function of holding tissue and organs in a given location to facilitate access and viewing is typically accomplished by a retractor. This instrumentation is ordinarily in the form of a broad paddle structure or multiple fingers attached to a handle. See, for example, U.S. Pat. No. 3,467,079 (James).

Endoscopic or laparoscopic procedures are characterized by the provision of an elongated cannula structure or trocar having a relatively small diameter with a proximal and distal end. The distal end is passed through the surrounding tissue into the body cavity via an incision in the body cavity. The trocar provides a conduit for the insertion of surgical instrumentation.

Collapsible intralumen expanders or retractors for endoscopic procedures have taken the form of radial fingers which are activatable to extend relative to each other upon entering the body cavity. A device for accomplishing such a task is disclosed in U.S. Pat. No. 5,195,505 to Josefsen. This patent describes a retractor structure showing a plurality of retractor blades mounted in a tubular housing. The blades are moveable between a closed position and an open position to facilitate ease of insertion and deployment through a trocar.

However, such endoscopic procedures are amenable to improvement. For example, each device in the endoscopic or laparoscopic procedure requires the use of a conventional trocar. The number of trocars that may be used during an operative procedure is limited in order to provide an uncluttered operating site, thereby minimizing available instrument access.

Percutaneous insertion techniques have been created in order to manipulate internal tissue where access to the body cavity is to be achieved through a very small percutaneous incision or puncture without necessitating the use of a trocar. For example, U.S. Pat. No. 5,106,369 (Christmas) discloses a needle instrument used with a flexible steel wire slidable within the needle. The flexible wire is provided with an atraumatic memory curved end which forms a hook upon being extended from the needle. The hook portion is employed to cradle and stabilize the umbilical cord and to permit the performance of various medical procedures on the umbilical cord. The distal end of the wire has an atraumatic tip to inhibit the puncture of the umbilical cord or other tissue.

However, this percutaneous structure is associated with a possibility of coring tissue upon insertion and the tissue thus removed may block the needle lumen and inhibit the deployment of the flexible wire.

There is, accordingly, a need for a new and improved surgical retractor to overcome the shortcomings and drawbacks of the above-mentioned prior art apparatus.

SUMMARY OF THE INVENTION

Briefly stated, the invention resides in the provision of a percutaneous surgical retractor having an outer sleeve structure with a proximal and distal end. The distal end of the outer sleeve has an open beveled configuration for percutaneous insertion. A blade is slidable within the outer sleeve. The retracting blade is moveable between at least a deployed position and a retracted position. The retracting blade is provided with a memory curved distal end. The retracting blade substantially closes the open beveled distal end of the outer sleeve when the blade is in the retracted position to inhibit the coring of tissue by the outer sleeve during percutaneous insertion. Structure is provided for deploying the retracting blade relative to the outer sleeve.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a percutaneous surgical retractor in accordance with one embodiment of the present invention.

FIG. 2 is a perspective view in partial cross section of a preferred embodiment of the present invention showing the retractor blade in the deployed position.

FIG. 2-A is a partial perspective view of the preferred embodiment of the present invention which includes a bifurcated hook configuration.

FIG. 2-B is a partial perspective view of preferred embodiment of the present invention which includes a trifurcated hook configuration.

FIG. 4 is a perspective view of the retractor blade in the retracted position.

FIG. 5 is a perspective view in cross section of the retractor blade assembly in a partially deployed position.

FIG. 6 is a perspective view of the retractor blade in the fully deployed position.

FIG. 7 is an end view of the outer sleeve-retractor blade assembly through line 7—7 of FIG. 4.

DETAILED DESCRIPTION OF PREFERRED EMBODIMENTS

Figure 3:
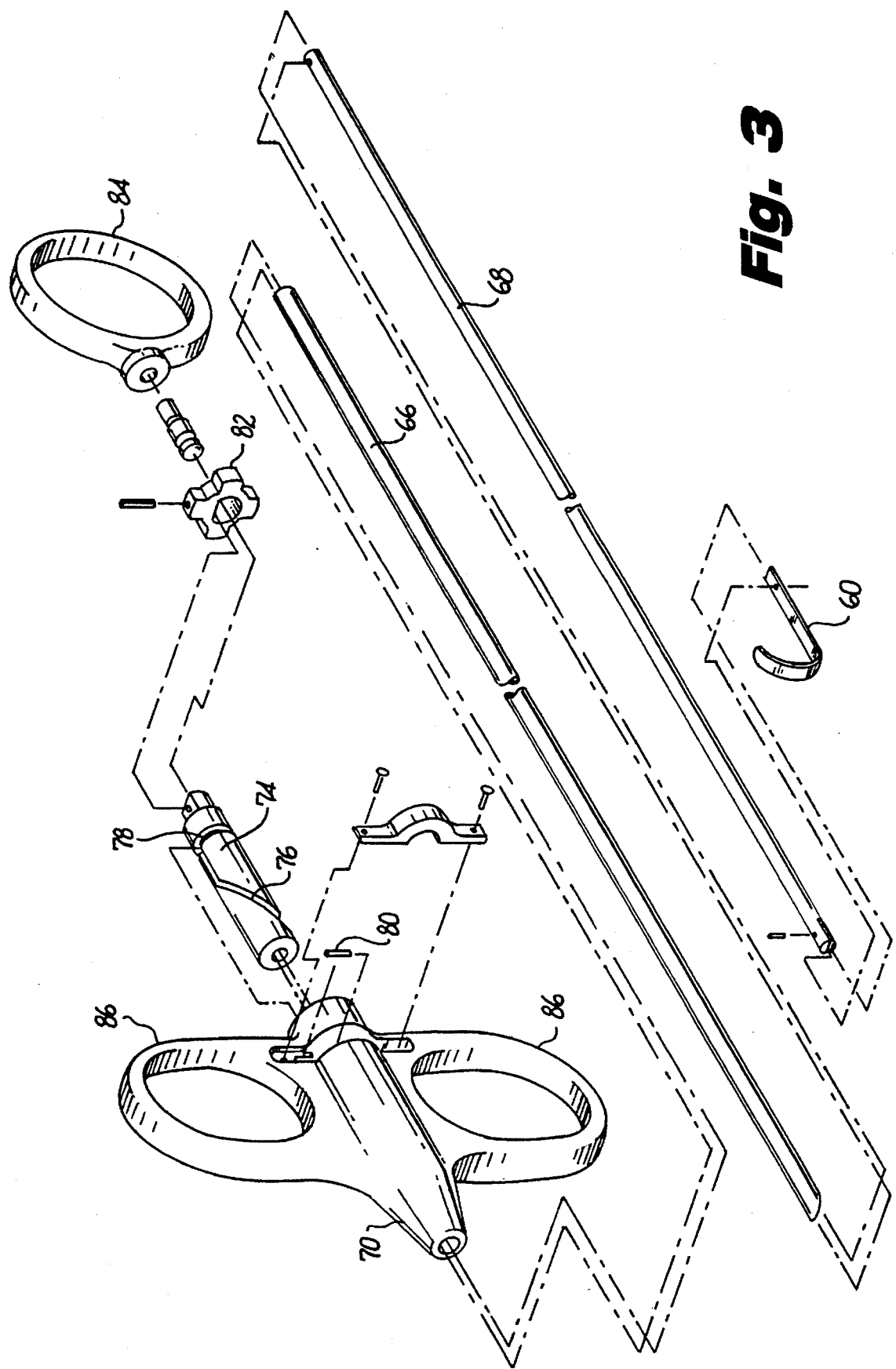
FIG. 3 is an exploded perspective view of a preferred embodiment of the present invention.

Referring now in specific detail to the drawings and in the description which follows, in which like reference numbers identify similar or identical elements, the term "proximal," as is traditional, will refer to the end of the surgical apparatus of the subject invention which is closest to the operator, while the term "distal" will refer to the end of the apparatus which is furthest from the operator.

FIGS. 1–2 illustrate a preferred embodiment of a surgical retractor, shown generally at 50. The retractor 50 can be broken down into a retractor blade assembly 52, elongated tubular housing means 54, and handle assembly 56. The embodiment of FIGS. 1–2 is adapted for and particularly useful in percutaneous procedures wherein at least a portion of the surgical retractor 50 is inserted directly into the operative site.

The retractor blade assembly 52 includes a blade 60 slidable within the distal insertion portion 64 of the tubular housing means 54. The retracting blade 60 is preferably formed of a resilient shape memory alloy, the configuration of which can be controlled mechanically by applying a stress to the material. The unstressed shape of the retracting blade 60 is a curved elbow configuration, and the retracting blade 60 acquires the shape when deployed from the distal insertion portion 64. The retracting blade 60 assumes the stressed position when retracted within the distal insertion portion 64. A preferred material of construction for blade 60 in a nickel-titanium alloy as described in U.S. Pat. No. 4,665,906, the contents of which are incorporated herein by reference.

Figure 8:
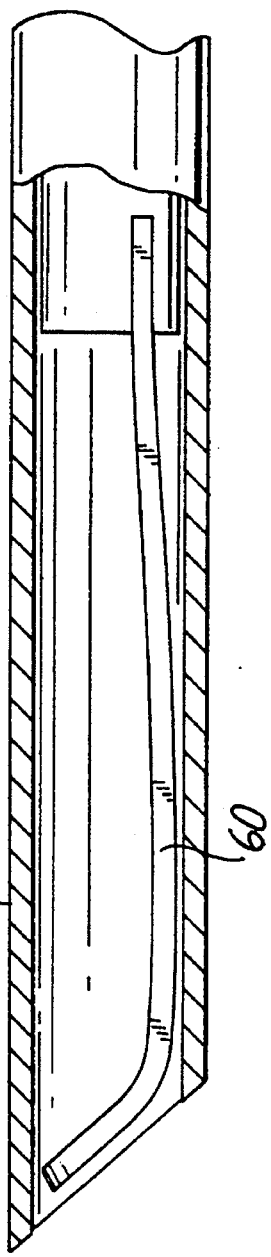
FIG. 8 is a side view in cross section of the outer sleeve-retractor blade assembly in the retracted position.

Referring to FIGS. 3–8, the distal insertion portion 64 is provided with an open beveled configuration forming a predetermined angle between 25° and 45° with the longitudinal axis (FIG. 8). In the retracted position, the retracting blade 60 is shaped to substantially block the opening of the distal insertion portion 64. (FIGS. 4, 7) The distal edge 62 of the retracting blade 60 is substantially circular. (FIG. 7)

Referring to FIGS. 1–3, the elongated tubular housing means 54 comprises an inner rod member 68 disposed within an outer sleeve 66. The distal end of the inner rod member 68 is attached to the proximal end of the retracting blade 60. The inner rod member 68 is coaxially slidable within the outer sleeve 66.

Referring to FIGS. 1–3, the handle assembly 56 comprises an axially aligned housing 70 having a central stepped bore 72 extending from a distal end to a proximal end. A barrel cam 92 is at least partially mounted in stepped bore 72 and configured for reciprocal longitudinal movement in the bore. The distal end of the barrel cam 74 is attached to the proximal end of the inner rod member 68. A helical channel 76 is formed in the barrel cam 74, and the proximal portion of the helical channel 76 intersects an annular channel 78 in the barrel cam 74. A transverse camming pin 80 is mounted in the housing 70 with a portion of the pin 80 extending into the stepped bore 72 to engage the helical channel 76. A pair of finger grips 86 are attached to the housing 70. An adjustment wheel 82 is attached to the proximal portion of the barrel cam 74. A thumb ring 84 is rotatably and coaxially connected to the proximal end of the barrel cam 74.

To operate the surgical retractor 50, the retracting blade 60 should be retracted within the distal insertion portion 64 such that the distal portion of the retracting blade 60 blocks the opening of the distal portion 64 (FIGS. 4, 7) This may be achieved by withdrawing the thumb ring 84 proximally with respect to the housing 70.

The beveled distal portion 64 is used to penetrate the abdomen, or other operative site. The configuration of the retracting blade 60 blocking the opening of the distal portion 64 acts to push tissue aside to create a narrow entrance incision rather than by coring tissue upon entrance with a substantially circular incision. To deploy the retracting blade 60 of this embodiment from the retracted position, thumb ting 84 is moved distally with respect to the housing 70. Engagement of the transverse camming pin 80 with the helical channel 76 of the barrel cam 74 imparts rotational motion to the barrel cam 74, the inner rod member 68, and the retracting blade 60 during deployment. (FIG. 5) Continued distal movement of the thumb ring 84 deploys the retracting blade 60 to assume its unstressed shape. (FIGS. 2, 6)

Subsequent distal movement is inhibited upon the engagement of the transverse camming pin 80 with the annular channel 78 in the barrel cam 74, upon reaching the proximal end of the helical channel 76. The annular channel 78 is oriented perpendicular to the longitudinal direction of movement of the barrel cam 74 and restrains the barrel cam 74 to rotational movement. The adjustment wheel 82 can be used to rotate the retracting blade 60 into position.

Alternative embodiments of the percutaneous retractor 50 of the subject invention are illustrated in FIGS. 2-A and 2-B. In the alternative embodiments, when the retracting blade is in an unstressed preformed position, the retracting blade 60 may be disposed in a bifurcated hook configuration 260, as shown in FIG. 2-A, or a trifurcated hook configuration 262, as shown in FIG. 2-B. The bifurcated and trifurcated configurations facilitate the engagement and deflection of tissue.

Figure 10:
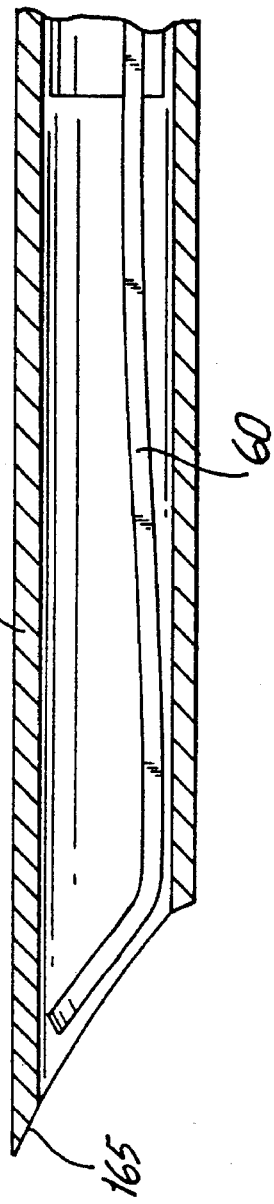
FIG. 10 is a side view in cross section of the present invention, shown in FIG. 9.
Figure 9:
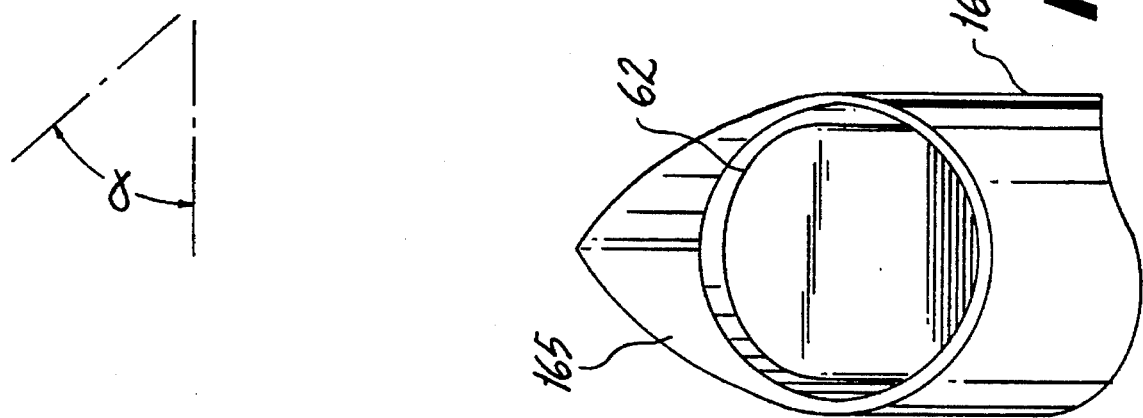
FIG. 9 is an end view of an embodiment of the present invention.

FIGS. 9–10 show another embodiment of the present invention. The distal insertion portion 164 of the outer sleeve 66 is shown having a sharpened edge 165. This embodiment is otherwise similar in operation to that of the distal insertion portion 64 described above.

The surgical retractor of the present invention is a compact, lightweight and easy to use instrument incorporating many features required during percutaneous surgical procedures which allows the surgeon to use the instrument with one hand thus freeing the other hand for manipulation of other instruments during surgery. The present retractor overcomes many of the disadvantages encountered with prior art devices and provides a precision instrument which is easy to handle and simple to manufacture. While the invention has been particularly shown and described with reference to preferred embodiments thereof, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A percutaneous surgical retractor comprising:

an outer sleeve defining a longitudinal axis and having a proximal end and a distal end, said distal end having an open beveled configuration defining a leading edge forming an angle with respect to the longitudinal axis of the outer sleeve to facilitate percutaneous insertion of the retractor;

a blade slidable within said outer sleeve between at least a deployed position extending beyond the distal end of the outer sleeve and a retracted position disposed within the outer sleeve, the blade having a memory curved distal end which, in the retracted position, assumes an orientation which approximates the angle of the leading edge of the open beveled end of the outer sleeve such that the distal end of said blade substantially closes said open beveled distal end of the outer sleeve when said blade is in said retracted position to inhibit coring of tissue by said outer sleeve during percutaneous insertion of said retractor; and means for deploying said blade relative to said outer sleeve.

2. A percutaneous surgical retractor as in claim 1 wherein said blade is moved distally into said deployed position relative to said outer sleeve by said deploying means.

3. A percutaneous surgical retractor as in claim 2 wherein said deploying means comprises a helical rotation structure operatively associated with said blade to change the angular orientation of said blade relative to said outer sleeve as said blade is moved between said deployed and retracted positions.

4. A percutaneous surgical retractor as in claim 1 wherein the memory curved distal end of said blade forms a hook when extended from the outer sleeve.

5. A percutaneous surgical retractor as in claim 1 wherein the memory curved distal end of said blade is provided with an atraumatic distal end.

6. A percutaneous surgical retractor as in claim 5 wherein said atraumatic distal end is configured in a substantially curvilinear shape to conform to an inner surface of said open beveled distal end of said outer sleeve.

7. A percutaneous surgical retractor as in claim 1 further comprising a handle assembly having a stepped longitudinal bore formed therein.

8. A percutaneous surgical retractor as in claim 7 wherein said means for deploying said blade comprises;

a barrel cam mounted in said stepped longitudinal bore and configured for reciprocal longitudinal movement therein;

an inner rod member attached at a distal end of said barrel cam, said blade being attached to a distal end of said inner rod member;

an actuation member attached to a proximal end of said barrel cam for reciprocal longitudinal movement of said barrel cam and said inner rod member relative to said handle, wherein as said actuation member is moved said blade is moved distally and rotationally relative to said outer sleeve.

9. A percutaneous surgical retractor as in claim 8, wherein said actuation member is a thumb ring rotatably and coaxially connected to the proximal end of said barrel cam.

10. A percutaneous surgical retractor as in claim 1 which further comprises means for rotational adjustment of said blade.

11. A percutaneous surgical retractor as in claim 10 wherein said rotational adjustment means comprises an adjustment wheel operatively associated with said blade to change the angular orientation of said blade.

12. A percutaneous surgical retractor as in claim 1 wherein the angle formed by the leading edge of said open beveled distal end of said outer sleeve forms a predetermined angle of about between 25° and 45° with respect to the longitudinal axis of said outer sleeve.

13. A percutaneous surgical retractor as in claim 1 wherein said open beveled distal end of said outer sleeve is provided with a sharpened edge.

14. A method of performing percutaneous retraction, comprising the steps of:

providing an outer sleeve defining a longitudinal axis and having a proximal end and a distal end, said distal end having an open beveled configuration defining a leading edge forming an angle with the longitudinal axis of the outer sleeve to facilitate percutaneous insertion of the retractor;

providing a blade slidable relative to said outer sleeve between at least a deployed position extending beyond the distal end of the outer sleeve and a retracted position disposed within the outer sleeve, the blade having a memory curved distal end which, in the retracted position, assumes an orientation which approximates the angle of the leading edge of the open beveled end of the outer sleeve such that said blade substantially closes said open beveled distal end of the outer sleeve when said blade is in said retracted position;

inserting said outer sleeve percutaneously while inhibiting coring of tissue with said distal end of said blade in said retracted position substantially closing said open beveled distal end of said outer sleeve; and deploying said blade relative to said outer sleeve to perform surgical retracting tasks.

15. The method of claim 14 wherein said deploying step comprises moving said blade distally into said deployed position relative to said outer sleeve.

16. The method of claim 15 wherein said deploying step further comprises changing the angular orientation of said blade relative to said outer sleeve as said blade is moved between said deployed and retracted positions.

17. The method of claim 14 wherein said deploying step comprises advancing said blade through the outer sleeve such that the memory curved end of said blade forms a hook when extended from the outer sleeve.

18. The method of claim 14 wherein the retractor further comprises means for rotational adjustment of said blade and the method includes changing angular orientation of said blade.

* * * * *